(12) United States Patent
Hefzi et al.

(10) Patent No.: US 11,242,510 B2
(45) Date of Patent: Feb. 8, 2022

(54) MAMMALIAN CELLS DEVOID OF LACTATE DEHYDROGENASE ACTIVITY

(71) Applicant: The Regents of the University of California, Oakland, CA (US)

(72) Inventors: Hooman Hefzi, Yorba Linda, CA (US); Nathan E. Lewis, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 509 days.

(21) Appl. No.: 16/096,784

(22) PCT Filed: May 1, 2017

(86) PCT No.: PCT/US2017/030380
§ 371 (c)(1),
(2) Date: Oct. 26, 2018

(87) PCT Pub. No.: WO2017/192437
PCT Pub. Date: Nov. 9, 2017

(65) Prior Publication Data
US 2019/0256824 A1   Aug. 22, 2019

Related U.S. Application Data

(60) Provisional application No. 62/330,409, filed on May 2, 2016.

(51) Int. Cl.
| | |
|---|---|
| *C12N 9/04* | (2006.01) |
| *A61K 39/395* | (2006.01) |
| *A61K 35/54* | (2015.01) |
| *C12N 5/00* | (2006.01) |
| *C12N 5/071* | (2010.01) |
| *C12N 9/12* | (2006.01) |
| *C12N 15/90* | (2006.01) |
| *C12P 21/00* | (2006.01) |

(52) U.S. Cl.
CPC ............ *C12N 9/0006* (2013.01); *A61K 35/54* (2013.01); *A61K 39/395* (2013.01); *C12N 5/00* (2013.01); *C12N 5/0682* (2013.01); *C12N 9/12* (2013.01); *C12N 15/907* (2013.01); *C12P 21/00* (2013.01); *C12Y 101/01027* (2013.01); *C12N 2310/20* (2017.05); *C12N 2501/71* (2013.01); *C12N 2510/02* (2013.01); *C12N 2800/80* (2013.01)

(58) Field of Classification Search
None
See application file for complete search history.

(56) References Cited

U.S. PATENT DOCUMENTS

2013/0084605 A1   4/2013   Zhou et al.

OTHER PUBLICATIONS

Chen et al., Engineering of a mammalian cell line for reduction of lactate formation and high monoclonal antibody production, Biot. Bioeng., 72(1):5555-5561 (2001).
Lee et al., Site-specific integration in CHO cells mediated by CRISPR/Cas9 and homology-directed DNA repair pathway, Sci. Repo., 5(1):1-11 (2015).
Xie et al., Targeting lactate dehydrogenase-a inhibits tumorigenesis and tumor progression in mouse models of lung cancer and impacts tumor-initiating cells, Cell Metab., 19(5):795-809 (2014).
Cai et al., Disruption of lactate dehydrogenase through homologous recombination to improve bioethanol production in Thermoanaerobacterium aotearoense, Enzyme and Microbial Technology. 48(2):155-161 (2011).
International Preliminary Report on Patentability for Corresponding International Application No. PCT/US17/30380, dated Nov. 15, 2018, 7 pages.
International Search Report and Written Opinion for Corresponding International Application No. PCT/US17/30380, dated Sep. 5, 2017, 9 pages.
Noh et al., Reduction of ammonia and lactate through the coupling of glutamine synthetase selection and downregulation of lactate dehydrogenase-A in CHO cells, Applied Microbiology and Biotechnology. 101(3):1035-1045 (2016).
Yip et al., Complete Knockout of the Lactate Dehydrogenase A Gene is Lethal in Pyruvate Dehydrogenase Kinase 1,2,3 Down-Regulated CHO Cells, Mol. Biotechnol. 56(9):833-888 (2014).
Zhou et al., Decreasing lactate level and increasing antibody production in Chinese Hamster Ovary Cells (CHO) by reducing the expression of lactate dehydrogenase and pyruvate dehydrogenase kinases, Journal of Biotechnol. 153(1-2):27-34 (2011).

*Primary Examiner* — Suzanne M Noakes
(74) *Attorney, Agent, or Firm* — Marshall, Gerstein & Borun LLP

(57) ABSTRACT

Provided are mammalian cells devoid of lactate dehydrogenase activity.

19 Claims, 13 Drawing Sheets

MAMMALIAN CELLS DEVOID OF LACTATE DEHYDROGENASE ACTIVITY

CROSS-REFERENCE TO RELATED APPLICATIONS

This application claims the benefit under 35 U.S.C. § 119(e) of U.S. Provisional Application No. 62/330,409, filed on May 2, 2016, which is hereby incorporated herein by reference in its entirety.

BACKGROUND

Lactate dehydrogenase activity catalyzes the interconversion of pyruvate and lactate and can be catalyzed by multiple enzymes which include gene products from genes including but not exclusive to LDHA, LDHB, LDHC in humans, mice, Ldha, Ldhb, Ldhc in mice and Chinese hamster cells, and many other homologous genes in other organisms. Herein, we use the human and Chinese hamster names interchangeably (e.g., LDHA and Ldha, LDHB and Ldhb, etc.) to refer to homologs of these genes. Despite several efforts by other groups, others have failed to completely remove lactate dehydrogenase, including LDHA and lactate dehydrogenase activity from mammalian cells. At best, others have only reduced lactate production.

U.S. Patent Publ. No. 2013/0084605 and Zhou, et al., *J Biotechnol.* (2011) 153(1-2):27-34 used siRNAs to knockdown Pdk (pyruvate dehydrogenase kinase, also sometimes abbreviated PDHK) isoforms 1, 2, 3 and LDHA, which reduced but did not eliminate expression of Pdk isoforms and LDHA. Yip, et al., *Mol Biotechnol.* (2014) 56(9):833-8 used siRNAs to knockdown Pdk 1, 2, and 3 then attempted unsuccessfully to knockout LDHA homozygously. Yip concluded that a complete knockout of LDHA is lethal in CHO cells, despite simultaneous down-regulation of PDK1, 2, and 3.

Toxic bioproducts such as lactate and ammonia have posed considerable challenges in bioprocessing since they limit cell growth and impact critical quality attributes of recombinant protein production (e.g., therapeutic drugs, enzymes). This is because lactate decreases pH in the culture and alters the regulation of biosynthetic enzymes. To mitigate the negative effects of lactic acid accumulation and control the culture pH, base is added to the media during the course of a bioprocess. However, the base addition increases osmolarity over time, which also negatively impacts the bioprocess by inhibiting growth and shortening the length of time in which the cells can produce the recombinant protein.

SUMMARY

In one aspect, provided is a viable mammalian cell completely and absolutely devoid of lactate dehydrogenase activity. In varying embodiments, the genes for:
i) lactate dehydrogenase A (LDHA) and/or lactate dehydrogenase B (LDHB); and ii) one or more of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out. In varying embodiments, the genes for: i) lactate dehydrogenase A (LDHA) and/or lactate dehydrogenase B (LDHB); and ii) two or more of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out. In some embodiments, the genes for: i) PDK1 and PDK2; ii) PDK1 and PDK3; iii) PDK1 and PDK4; iv) PDK2 and PDK3; v) PDK2 and PDK4; or vi) PDK3 and PDK4 are not expressed, rendered non-functional, eliminated and/or homozygously knocked out. In varying embodiments, the genes for: i) lactate dehydrogenase A (LDHA) and/or lactate dehydrogenase B (LDHB); and ii) three or more of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out. In varying embodiments, the genes for: i) PDK1, PDK2 and PDK3; ii) PDK1, PDK2 and PDK4; iii) PDK1, PDK3 and PDK4; or iv) PDK2, PDK3 and PDK4; are not expressed, rendered non-functional, eliminated and/or homozygously knocked out. In varying embodiments, the genes for: i) lactate dehydrogenase A (LDHA) and/or lactate dehydrogenase B (LDHB); and ii) all of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out. In some embodiments, the cell is a Chinese Hamster Ovary (CHO) cell. In some embodiments, the cell further comprises one or more heterologous polynucleotides encoding one or more recombinant polypeptides of interest. In some embodiments, the cell further comprises one or more expression cassettes comprising one or more heterologous polynucleotides encoding one or more recombinant polypeptides of interest. In some embodiments, the one or more heterologous polynucleotides are integrated into the genome of the cell. In some embodiments, the one or more heterologous polynucleotides are in a plasmid or an episomal vector. In some embodiments, the one or more recombinant polypeptides of interest comprise a therapeutic polypeptide. In varying embodiments, the therapeutic polypeptide comprises an antibody or antibody fragment, an enzyme, a cytokine, or a hormone.

In a further aspect, provided is a population of cells, wherein each cell in the population is a mammalian cell that does not express LDHA and/or LDHB, and does not express one, two, three or four of PDK1, PDK2, PDK3 and PDK4, wherein the cells produce no detectable lactate.

In a related aspect, provided is an in vitro cell culture comprising a population of cells, wherein each cell in the population is a mammalian cell that does not express LDHA and/or LDHB; and does not express one, two, three or four of PDK1, PDK2, PDK3 and PDK4, wherein the cells produce no detectable lactate. In some embodiments, the population of cells comprises viable mammalian cells at a density of at least about $13 \times 10^6$ cells/ml, e.g., at least about $14 \times 10^6$ cells/ml, $15 \times 10^6$ cells/ml, $16 \times 10^6$ cells/ml, $17 \times 10^6$ cells/ml, or higher. In varying embodiments, the culture comprises accumulated added base at a concentration of less than about 5 mOsm/kg, e.g., less than about 4.5 mOsm/kg, 4 mOsm/kg, 3.5 mOsm/kg, or 3 mOsm/kg, after at least about 5 days of culture. In some embodiments, the culture comprises no detectable lactate.

In a further aspect, provided is a method of making a viable mammalian cell devoid of lactate dehydrogenase activity. In varying embodiments, the method comprises homozygously knocking out, rendering non-functional, and/or eliminating in the cell the genes for LDHA and/or LDHB, and the genes for one or more of PDK1, PDK2, PDK3 and PDK4. In varying embodiments, the method comprises homozygously knocking out, rendering non-functional, and/or eliminating in the cell the genes for LDHA and/or LDHB, and the genes for two or more of PDK1, PDK2, PDK3 and PDK4. In some embodiments, the genes for: i) PDK1 and PDK2; ii) PDK1 and PDK3; iii) PDK1 and PDK4; iv) PDK2 and PDK3; v) PDK2 and PDK4; or vi) PDK3 and PDK4 are not expressed, rendered non-functional, eliminated and/or homozygously knocked out. In varying embodiments, the method comprises homozygously knocking out, rendering non-functional, and/or eliminating in the cell the genes for LDHA and/or LDHB, and the genes for three or more of PDK1, PDK2, PDK3 and PDK4. In some embodiments, the genes for: i) PDK1, PDK2 and PDK3; ii) PDK1, PDK2 and PDK4; iii) PDK1, PDK3 and PDK4; or iv) PDK2, PDK3 and PDK4; are not expressed, rendered non-functional, eliminated and/or homozygously knocked out. In varying embodiments, the methods comprise homozygously knocking out, rendering non-functional, and/or eliminating in the cell the genes for LDHA and/or LDHB, and the genes for all of PDK1, PDK2, PDK3 and PDK4.

In a further aspect, provided is a method for eliminating lactate production in cultured mammalian cells. In varying embodiments, the method comprises culturing a population of cells, wherein each cell in the population is a mammalian cell that does not express LDHA and/or LDHB; and does not express one, two, three or four of PDK1, PDK2, PDK3 and PDK4, wherein the cells produce no detectable lactate.

In a further aspect, provided is a method of producing a recombinant polypeptide. In varying embodiments, the methods comprises culturing a population of cells under conditions that allow the cells to produce the recombinant polypeptide, wherein each cell in the population is a mammalian cell that comprises a heterologous polynucleotide encoding the recombinant polypeptide and that does not express LDHA and/or LDHB; and does not express one, two, three or four of PDK1, PDK2, PDK3 and PDK4, wherein the cells produce no detectable lactate.

In another aspect, provided is a method of increasing the production of a recombinant polypeptide. In varying embodiments, the methods comprises culturing a population of cells under conditions that allow the cells to produce the recombinant polypeptide, wherein each cell in the population is a mammalian cell that comprises a heterologous polynucleotide encoding the recombinant polypeptide and that does not express LDHA and/or LDHB; and does not express one, two, three or four of PDK1, PDK2, PDK3 and PDK4, wherein the cells produce no detectable lactate, whereby the yield of recombinant polypeptide is increased in comparison to the yield of recombinant polypeptide produced by a wild-type cell or a control mammalian cell having lactate dehydrogenase and/or pyruvate dehydrogenase kinase activity. In some embodiments, the production of recombinant polypeptide is increased by at least about 70% higher, about 71% higher, about 75% higher, about 80% higher, about 85% higher, about 90% higher, about 95% higher, about 100% higher, about 125% higher, about 150%, about 200% higher, about 250% higher, about 300% higher, about 350% higher, about 400% higher, about 450% higher, about 500 higher, about 550% higher, about 600% higher, about 650% higher, about 700% higher, about 750% higher, or about 800% higher, or more, in comparison to the yield of recombinant polypeptide produced by a wild-type cell or a control mammalian cell having lactate dehydrogenase and/or pyruvate dehydrogenase kinase activity.

With respect to the embodiments of the methods, in some embodiments, the base is not needed to control the pH of the culture. In some embodiments, the culture comprises accumulated added base at a concentration of less than about 5 mOsm/kg, e.g., less than about 4.5 mOsm/kg, 4 mOsm/kg, 3.5 mOsm/kg, or 3 mOsm/kg, after at least about 5 days of culture. In some embodiments, lactate is not detectable in the culture. In some embodiments, the cell density in the culture is at least about $13 \times 10^6$ cells/ml, e.g., at least about $14 \times 10^6$ cells/ml, $15 \times 10^6$ cells/ml, $16 \times 10^6$ cells/ml, $17 \times 10^6$ cells/ml, or higher. In some embodiments, the mammalian cell is a Chinese Hamster Ovary (CHO) cell.

Definitions

As used herein, the term "cells in culture" or "cultured cells" refers two or more cells in a solution (e.g., a cell medium) that allows the cells to undergo one or more cell divisions.

The term "polynucleotide" or "nucleic acid," as used interchangeably herein, refers to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs.

The term "heterologous nucleic acid" or "heterologous polypeptide" refers to a nucleic acid or a polypeptide whose sequence is not identical to that of another nucleic acid or polypeptide naturally found in the same host cell.

As used herein, "operably linked" as used herein refers to a functional relationship between two or more nucleic acid (e.g., DNA) segments. Typically, it refers to the functional relationship of transcriptional regulatory sequence to a transcribed sequence. For example, a promoter is operably linked to a coding sequence, such as a heterologous polynucleotide encoding a polypeptide of interest (e.g., a therapeutic polypeptide, e.g., an antibody or antibody fragment), if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term "promoter" includes all sequences capable of driving transcription of a coding sequence in a cultured cell, e.g., a mammalian cell. Thus, promoters used in the expression cassettes described herein include cis-acting transcriptional control elements and regulatory sequences that are involved in regulating or modulating the timing and/or rate of transcription of a gene.

As used herein, "vector" means a construct, which is capable of delivering, and preferably expressing, one or more gene(s) or sequence(s) of interest (e.g., a therapeutic polypeptide) in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. Suitable vectors are those which are compatible with the host cell employed. Suitable vectors can be derived, for example, from a bacterium, a virus (such as bacteriophage T7 or a M-13 derived phage), a cosmid, a yeast, or a plant. Protocols for obtaining and using such vectors are known to those in the art (see, for example, Green and Sambrook, Molecular Cloning: A Laboratory Manual, 4th ed., Cold Spring Harbor, 2012).

The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The term "osmolality" refers to the number of solute particles dissolved in 1 liter of solution. Solutes which can be added to the culture medium so as to increase the osmolality thereof include proteins, peptides, amino acids, non-metabolized polymers, vitamins, ions, salts (e.g., sodium or potassium salts), sugars, metabolites, organic acids, lipids, etc. When used herein, the abbreviation "mOsm" means "milliosmoles/Liter $H_2O$."

As used herein, a "host cell" includes an individual cell, cultured cells, or cell in culture that can be or has been a recipient for vector(s) or siRNA(s) for incorporation of polynucleotide inserts to produce polypeptide. Host cells include progeny of a single cultured cell, and the progeny may not necessarily be completely identical (in morphology or in genomic DNA complement) to the original parent cell due to natural, accidental, or deliberate mutation.

The term "therapeutic polypeptide" refers to a polypeptide having therapeutic pharmacological activity in a mammal.

The phrases "increased polypeptide yield" or "increased polypeptide production" or "increased polypeptide expression" interchangeably refer to increased production of a recombinant polypeptide of interest from a viable mammalian cell or population of viable mammalian cells devoid of lactate dehydrogenase activity, in comparison to production of the same recombinant polypeptide of interest from a mammalian cell or population of mammalian cells that have detectable lactate dehydrogenase activity. The increased production of the recombinant polypeptide from the viable mammalian cell or population of viable mammalian cells devoid of lactate dehydrogenase activity can be at least about 10%, e.g., at least about 15%, 20%, 25%, 30%, 35%, 40%, 50%, 60%, 70%, 80%, 90%, 100%, 150%, 200%, 250%, 300%, 400%, 500%, 600%, 700%, 800%, 900%, 1000%, or more, in comparison to production of the same recombinant polypeptide of interest from a mammalian cell or population of mammalian cells that have detectable lactate dehydrogenase activity.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The term "antibody" is used in the broadest sense and specifically covers monoclonal antibodies (including full length monoclonal antibodies), polyclonal antibodies, multispecific antibodies (e.g., bispecific antibodies), and antibody fragments.

"Antibody fragments" comprise a portion of a full length antibody, generally the antigen binding or variable region thereof. Examples of antibody fragments include Fab, Fab', F(ab')$_2$, and Fv fragments; single-chain antibody molecules; diabodies; linear antibodies; and multispecific antibodies formed from antibody fragments.

The immunoglobulin (antibody) structure can be a tetramer (e.g., having two heavy chains and two light chain) or a dimer (e.g., having two heavy chains, such as a camelid antibody). Typically, each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879-5883. While the VH and VL are connected to each as a single polypeptide chain, the VH and VL domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) Protein Eng. 8: 1323-1331).

Unless otherwise indicated, conventional techniques of molecular biology (including recombinant techniques), microbiology, cell biology, biochemistry and immunology, which are within the skill of the art, are employed. Such techniques are explained fully in the literature, such as, Molecular Cloning: A Laboratory Manual, fourth edition (Green and Sambrook 2012) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987-2016); PCR: The Polymerase Chain Reaction, (Mullis et al., eds., 1994); Current Protocols in Immunology (J. E. Coligan et al., eds., 1991-2016); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

DETAILED DESCRIPTION

1. Introduction

Figure 1:
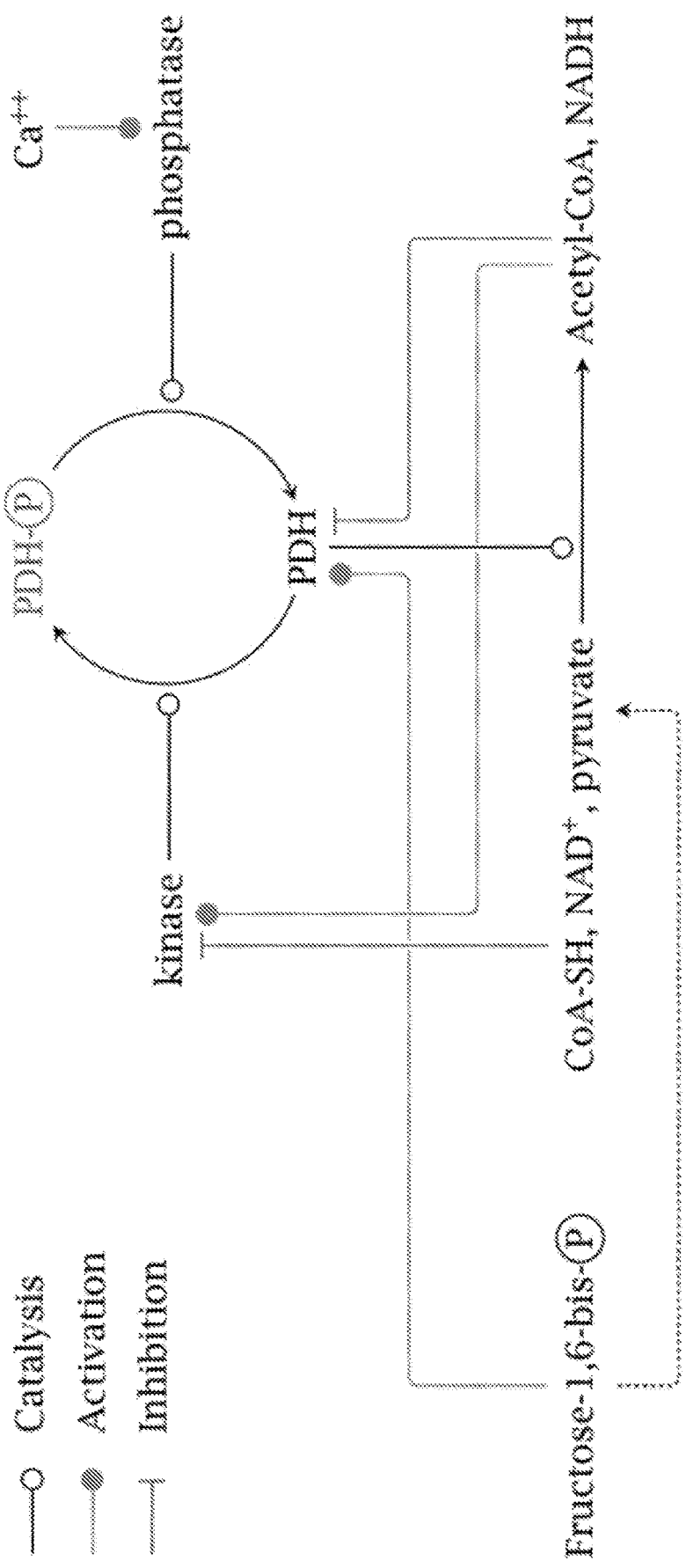
FIG. 1 depicts overview of regulation of the PDH complex by PDKs. The products of the PDH reaction activate PDKs, which inhibit PDH via phosphorylation. The inhibition of the PDKs by substrates of the PDH enzyme is also shown, however this inhibition appears to be insufficient for normal PDH activity. Figure from watcut.uwaterloo.ca/webnotes/Metabolism/pdhRegulation.html.

Provided herein are mammalian cells that are completely devoid of lactate dehydrogenase activity, produce zero lactate, and that can be cultured at higher maximum cell density while growing at a normal rate (e.g., compared to the wildtype mammalian cell cell). In certain embodiments, the mammalian cells are simultaneous or concurrent homozygous knockouts of the LDHA (lactate dehydrogenase A isoform) and/or LDHB (lactate dehydrogenase B isoform) genes and one, two, three or four of PDK1, PDK2, PDK3 and PDK4.

Lactate production can be completely eliminated via a homozygous knockout of LDHA and/or LDHB genes and one, two, three or four of PDK1, PDK2, PDK3 and PDK4. Cells with LDHA knocked-out and having with fewer than four Pdk isoform genes also knocked out were screened, and such cells also had no detectable lactate production. However, LDHA knock-out cells having fewer than four of the Pdk isoforms also knocked-out showed reduced mRNA expression of the remaining Pdk genes and inferior bioprocess attributes, such as reduced growth rate. The methods and mammalian cells described herein allow for increased yields and efficiency for recombinant protein (e.g., including therapeutic proteins) production from mammalian cells.

2. Mammalian Cells and Populations of Mammalian Cells

Provided is a viable mammalian cell or a population of viable mammalian cells, each cell in the population being completely and absolutely devoid of lactate dehydrogenase activity.

In varying embodiments, the viable mammalian cell or a population of viable mammalian cells completely and absolutely do not express (i.e., are devoid of expression of) any of (i.e., express none of): lactate dehydrogenase A (LDHA) and/or lactate dehydrogenase B (LDHB); and further do not express one, two, three or four of PDK1, PDK2, PDK3 and PDK4.

In varying embodiments, the genes for LDHA and/or LDHB; and the genes for one, two, three or four of PDK1, PDK2, PDK3 and PDK4 are homozygously knocked out, rendered non-functional and/or eliminated. In some embodiments, the cell or each member of the population of cells is a Chinese Hamster Ovary (CHO) cell.

In some embodiments, the cell further comprises one or more heterologous polynucleotides encoding one or more recombinant polypeptides of interest. In some embodiments, the cell further comprises one or more expression cassettes comprising one or more heterologous polynucleotides encoding one or more recombinant polypeptides of interest. In some embodiments, the one or more heterologous polynucleotides are integrated into the genome of the cell. In some embodiments, the one or more heterologous polynucleotides are in a plasmid or an episomal vector. In some embodiments, the one or more recombinant polypeptides of interest comprise a therapeutic polypeptide. In varying embodiments, the therapeutic polypeptide comprises an antibody or antibody fragment, an enzyme, a cytokine, or a hormone.

Lactate dehydrogenase A (LDHA) converts pyruvate into lactate. The accession numbers of exemplary LDHA polynucleotides and polypeptides include, but are not limited to, NM_001244050.1→NP_001230979.1 (Chinese Hamster LDHA), NM_005566.3→NP_005557.1 (human LDHA isoform 1), NM_001135239.1→NP_001128711.1 (human LDHA isoform 2), NM_001165414.1→NP_001158886.1 (human LDHA isoform 3), NM_001165415.1→NP_001158887.1 (human LDHA isoform 4), NM_001165416.1→NP_001158888.1 (human LDHA isoform 5), NM_010699.2→NP_034829.1 (mouse LDHA isoform 1), NM_001136069.2→NP_001129541.2 (mouse LDHA isoform 2), and NM_017025.1→NP_058721.1 (rat LDHA).

Lactate dehydrogenase B (LDHB) converts pyruvate into lactate. The accession numbers of exemplary LDHB polynucleotides and polypeptides include, but are not limited to human isoforms NM_001174097.2→NP_001167568.1; NM_001315537.1→NP_001302466.1; and NM_002300.7→NP_002291.1. Polynucleotides and polypeptides for Chinese Hamster LDHB include, e.g., XM_007643790.1→XP_007641980.1 and XM_007624678.1→XP_007622868.1. Polynucleotides and polypeptides for mouse LDHB include, e.g., NM_001302765.1→NP_001289694.1; NM_001316322.1→NP_001303251.1; NM_008492.3→NP_032518.1. Polynucleotides and polypeptides for rat LDHB include, e.g., NM_001316333.1→NP_001303262.1; NM_001316334.1→NP_001303263.1; and NM_012595.2→NP_036727.1.

In producing the present LDH-deficient mammalian cells, genomic DNA encoding LDHA and/or LDHB native to the mammalian cell can be targeted for disruption and/or elimination, e.g., using CRISPR/Cas9 and a guide RNA that specifically hybridizes to the LDHA and/or LDHB genes, respectively.

Standard methods known by persons skill in the art can be used to determine whether a mammalian cell comprises a lactate dehydrogenase (LDH) polypeptide, and whether the LDH polypeptide has LDH activity by measuring the ability of the polypeptide to convert pyruvate into lactate in vitro, in a cell extract, or in vivo. Such in vitro cell lysate LDH detection assays include immunoassays (e.g., ELISA, Western Blots) and activity assays are demonstrated herein, e.g., in FIGS. 5 and 6. In vitro assays for detecting lactate dehydrogenase activity are known in the art and described, e.g., in Baba, et al., *Antivir Chem Chemother.* 2005; 16(1):33-9; Larson, *J Dairy Res.* (2005) 72(2):209-16; and Mori, et al., *Tohoku J Exp Med.* 1995 December; 177(4):315-25.

Pyruvate dehydrogense kinase (PDK) inhibits the conversion of pyruvate into acetyl-CoA. The accession numbers of exemplary PDK1 polypeptides and nucleic acids include, but are not limited to, NM_172665.5→NP_766253.2 (mouse PDK1), L42450 (human), and BC089783 (rat). The accession numbers of exemplary PDK2 polypeptides and nucleic acids include, but are not limited to, NM_002611.4→NP_002602.2 (human PDK2 isoform 1), NM_001199898.1→NP_001186827.1 (human PDK2 isoform 2), NM_001199899.1→NP_001186828.1 (human PDK2 isoform 2), NM_001199900.1→NP_001186829.1 (human PDK2 isoform 3), NM_030872 (rat), and NM_133667 (mouse). The accession numbers of exemplary PDK3 polypeptides and nucleic acids include, but are not limited to, NM_001142386.2→NP_001135858.1 (human PDK3 isoform 1), NM_005391.4→NP_005382.1 (human PDK3 isoform 2), BC169078 (rat PDK3), and NM_145630 (mouse PDK3). The accession numbers of exemplary PDK4 polypeptides and nucleic acids include, but are not limited to, NM_002612 (human PDK4), NM_053551 (rat PDK4), and NM_013743.2→NP_038771.1 (mouse PDK4). Polynucleotides and polypeptides for Chinese Hamster PDK include, e.g., gene ID 100774056, Refseq XM_007645579.2→XP_007643769.1 or XM_007645572.2→XP_007643762.1 or XM_007611707.1→XP_007609897.1 and XM_007611708.2→XP_007609898.1.

Standard methods known by person skilled in the art can be used to determine whether a PDK polypeptide has PDK activity by measuring the ability of the polypeptide to inhibit the conversion of pyruvate into acetyl-CoA in vitro, in a cell extract, or in vivo. In vitro assays for detecting pyruvate dehydrogenase kinase activity are known in the art and described, e.g., in Kerbey, et al., *Biochem J.* 1982 Jul. 15; 206(1):103-11.

3. Recombinant Polypeptides of Interest

Viable mammalian cells that are devoid of lactate dehydrogenase activity can grow in cell culture at higher densities than wild-type or control counterpart cells that have detectable lactate dehydrogenase activity. Accordingly, viable mammalian cells that are devoid of lactate dehydrogenase activity are useful for the increased production yield of a recombinant polypeptide of interest expressed from the cells. Recombinant polypeptides of interest include therapeutic polypeptides, e.g., antibody and antibody fragments, enzymes, cytokines (e.g., an interferon, an interleukin, a chemokine) and hormones (e.g., insulin).

a. Antibodies

In varying embodiments, the therapeutic polypeptide is an antibody, antibody fragment or immunoadhesin. Techniques for generating such molecules are discussed below.

Antibodies of interest for recombinant expression from mammalian cells devoid of lactate dehydrogenase activity include without limitation: anti-CD20 antibodies such as chimeric anti-CD20 "C2B8" as in U.S. Pat. No. 5,736,137 (RITUXAN™); anti-VEGF antibodies, including humanized and/or affinity matured anti-VEGF antibodies such as the humanized anti-VEGF antibody huA4.6.1 AVASTIN™ (Kim et al., Growth Factors, 7:53-64 (1992), International Publication No. WO 96/30046, and WO 98/45331, published Oct. 15, 1998) and V3LA; anti-MUC16 antibody; anti-CD4 antibodies such as the cM-7412 antibody (Choy et al. Arthritis Rheum. 39(1):52-56 (1996)) and the Ibalizumab (TNX355) antibody; anti-MET antibodies such as one-armed 5D5 anti-C-Met antibody; anti-HER2 antibodies Trastuzumab (HERCEPTIN) (Carter et al., Proc. Natl. Acad. Sci. USA, 89:4285-4289 (1992), U.S. Pat. No. 5,725,856) and humanized 2C4 (WO01/00245, Adams et al.), a chimeric or humanized variant of the 2H7 antibody as in U.S. Pat. No. 5,721,108B1, or Tositumomab (BEXXAR™); anti-IL-8 antibodies (St John et al., Chest, 103:932 (1993), and International Publication No. WO 95/23865); anti-prostate stem cell antigen (PSCA) antibodies (WO01/40309); anti-CD40 antibodies, including S2C6 and humanized variants thereof (WO00/75348); anti-CD1 antibodies (U.S. Pat. No. 5,622,700, WO 98/23761, Steppe et al., Transplant Intl. 4:3-7 (1991), and Hourmant et al., Transplantation 58:377-380 (1994)); anti-CD18 (U.S. Pat. No. 5,622,700, issued Apr. 22, 1997, or as in WO 97/26912, published Jul. 31, 1997); anti-IgE antibodies (including E25, E26 and E27; U.S. Pat. No. 5,714,338, issued Feb. 3, 1998 or U.S. Pat. No. 5,091,313, issued Feb. 25, 1992, WO 93/04173 published Mar. 4, 1993, or International Application No. PCT/US98/13410 filed Jun. 30, 1998, U.S. Pat. No. 5,714,338, Presta et al., J. Immunol. 151:2623-2632 (1993), and International Publication No. WO 95/19181); anti-Apo-2 receptor antibodies (WO 98/51793 published Nov. 19, 1998); anti-TNF-.alpha. antibodies, including cA2 (REMICADE™), CDP571 and MAK-195 (See, U.S. Pat. No. 5,672,347 issued Sep. 30, 1997, Lorenz et al. J. Immunol. 156(4):1646-1653 (1996), and Dhainaut et al. Crit. Care Med. 23(9):1461-1469 (1995)); anti-Tissue Factor (TF) antibodies (European Patent No. 0 420 937 B1 granted Nov. 9, 1994); anti-human .alpha.4.beta.7 integrin antibodies (WO 98/06248 published Feb. 19, 1998); anti-epidermal growth factor receptor (EGFR) antibodies (e.g. chimerized or humanized 225 antibody as in WO 96/40210 published Dec. 19, 1996); anti-CD3 antibodies such as OKT3 (U.S. Pat. No. 4,515,893 issued May 7, 1985); anti-CD25 or anti-Tac antibodies such as CHI-621 (SIMULECT™ and ZENAPAX™ (See U.S. Pat. No. 5,693,762 issued Dec. 2, 1997); anti-CD52 antibodies such as CAMPATH-1H (Riechmann et al. Nature 332:323-337 (1988)); anti-Fc receptor antibodies such as the M22 antibody directed against Fcy RI as in Graziano et al. J. Immunol. 155(10):4996-5002 (1995); anti-carcinoembryonic antigen (CEA) antibodies such as hMN-1 4 (Sharkey et al. Cancer Res. 55(23Suppl): 5935s-5945s (1995); antibodies directed against breast epithelial cells including huBrE-3, hu-Mc 3 and CRL6 (Ceriani et al. Cancer Res. 55(23): 5852s-5856s (1995); and Richman et al. Cancer Res. 55(23 Supp): 5916s-5920s (1995)); antibodies that bind to colon carcinoma cells such as C242 (Litton et al. Eur J Immunol. 26(1): 1-9 (1996)); anti-CD38 antibodies, e.g. AT 13/5 (Ellis et al. J. Immunol. 155(2):925-937 (1995)); anti-CD33 antibodies such as Hu M195 (Jurcic et al. Cancer Res 55(23 Suppl):5908s-5910s (1995) and CMA-676 or CDP771); anti-CD22 antibodies such as LL2 or LymphoCide (Juweid et al. Cancer Res 55(23 Suppl):5899s-5907s (1995)); anti-EpCAM antibodies such as 17-1A (PANOREX™); anti-GpIIb/IIIa antibodies such as abciximab or c7E3 Fab (REOPRO™); anti-RSV antibodies such as MEDI-493 (SYNAGIS™); anti-CMV antibodies such as PROTOVIR™; anti-HIV antibodies such as PRO542; anti-hepatitis antibodies such as the anti-Hep B antibody OSTAVIR™; anti-CA 125 antibodies, such as OvaRex; anti-idiotypic GD3 epitope antibody BEC2; anti-.alpha.v.beta.3 antibodies, including VITAXIN™; anti-human renal cell carcinoma antibody such as ch-G250; ING-1; anti-human 17-1A antibody (3622W94); anti-human colorectal tumor antibody (A33); anti-human melanoma antibody R24 directed against GD3 ganglioside; anti-human squamous-cell carcinoma (SF-25); and anti-human leukocyte antigen (HLA) antibodies such as Smart ID10 and the anti-HLA DR antibody Oncolym (Lym-1).

Aside from the antibodies specifically identified above, the skilled practitioner can generate antibodies directed against an antigen of interest, e.g., using the techniques well known in the art, e.g., described in Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); and The Antibodies (M. Zanetti and J. D. Capra, eds., Harwood Academic Publishers, 1995).

b. Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

c. Antibody Fragments

Various techniques have been developed for the production of antibody fragments. Traditionally, these fragments were derived via proteolytic digestion of intact antibodies (see, e.g., Morimoto et al. Journal of Biochemical and Biophysical Methods 24:107-117 (1992) and Brennan et al., Science, 229:81 (1985)). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')2 fragments (Carter et al., Bio/Technology 10:163-167 (1992)). According to another approach, F(ab')2 fragments can be isolated directly from recombinant host cell culture. A single chain Fv fragment (scFv) can also be isolated. See WO 93/16185. Other techniques for the production of antibody fragments will be apparent to the skilled practitioner.

d. Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytic ally cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from E. coli, which can be chemically coupled to form bispecific antibodies. Shalaby et al., J. Exp. Med., 175: 217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10):1057-1062 (1995). Briefly, these antibodies comprise a pair of tandem Fd segments (VH-CH1-VH and VL) which form a pair of antigen binding regions. Linear antibodies can be bispecific or monospecific.

Antibodies with more than two valencies are contemplated. For example, trispecific antibodies can be prepared. Tutt et al. J. Immunol. 147: 60 (1991).

e. Immunoadhesins

In varying embodiments, the therapeutic polypeptide is an immunoadhesin. The simplest and most straightforward immunoadhesin design combines the binding domain(s) of the adhesin (e.g., the extracellular domain (ECD) of a receptor) with the hinge and Fc regions of an immunoglobulin heavy chain. Ordinarily, when preparing the immunoadhesins, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion, or binding characteristics of the immunoadhesin.

In some embodiments, the adhesin sequence is fused to the N-terminus of the Fc domain of immunoglobulin G1 (Ig G0. It is possible to fuse the entire heavy chain constant region to the adhesin sequence. However, preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In some embodiments, the adhesin amino acid sequence is fused to (a) the hinge region and or CH2 and CH3 or (b) the CH1, hinge, CH2 and CH3 domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g., Aruffo et al., Cell 61:1303-1313 (1990); and Stamenkovic et al., Cell 66:1133-1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

4. Cell Cultures

Further provided are in vitro cell cultures comprising a population of cells, wherein each cell in the population is a mammalian cell that does not express LDHA and/or LDHB; and does not express one, two, three or four of PDK1, PDK2, PDK3 and PDK4. In some embodiments, the cell culture comprises viable mammalian cells at a density of at least about $13\times10^6$ cells/ml, e.g., at least about $14\times10^6$ cells/ml, $15\times10^6$ cells/ml, $16\times10^6$ cells/ml, $17\times10^6$ cells/ml, or higher. In varying embodiments, the culture comprises accumulated added base at a concentration of less than about 5 mOsm/kg, e.g., less than about 4.5 mOsm/kg, 4 mOsm/kg, 3.5 mOsm/kg, or 3 mOsm/kg, after at least about 5 days of culture. In varying embodiments, the cultures comprise no added base, after at least about 5 days of culture. In some embodiments, the culture comprises no detectable lactate.

5. Methods of Eliminating Lactate Production in Mammalian Cells

Provided are methods for eliminating the production of lactate in cultured mammalian cells and of making a viable mammalian cell population wherein each cell is devoid of lactate dehydrogenase activity. In varying embodiments, the methods comprise culturing a population of cells, wherein each cell in the population is a mammalian cell that does not express LDHA and/or LDHB; and does not express one, two, three or four of PDK1, PDK2, PDK3 and PDK4, wherein the cells produce no detectable lactate. In varying embodiments, the method comprises homozygously knocking out, rendering non-functional, and/or eliminating in the cell the genes for LDHA and/or LDHB; and the genes for one, two, three or four of PDK1, PDK2, PDK3 and PDK4. In varying embodiments, the methods comprise homozygously knocking out, rendering non-functional, and/or eliminating in the cell the genes using CRISPR/Cas9, e.g., and guide RNAs (gRNAs) that specifically hybridize to the genes the genes encoding LDHA and/or LDHB; and the genes encoding one, two, three or four of PDK1, PDK2, PDK3 and PDK4.

6. Methods of Expressing Recombinant Polypeptides

Further provided are methods of producing a recombinant polypeptide, including the therapeutic polypeptides described above and herein. The polypeptide (e.g., antibody) to be produced using the methods described herein can be produced using recombinant techniques known in the art. In varying embodiments, the methods comprises culturing a population of cells under conditions that allow the cells to produce the recombinant polypeptide, wherein each cell in the population is a mammalian cell that comprises a heterologous polynucleotide encoding the recombinant polypeptide and that does not express LDHA and/or LDHB; and does not express one, two, three or four of PDK1, PDK2, PDK3 and PDK4, wherein the cells produce no detectable lactate.

Also provided are methods of increasing the production of a recombinant polypeptide. In varying embodiments, the methods comprises culturing a population of cells under conditions that allow the cells to produce the recombinant polypeptide, wherein each cell in the population is a mammalian cell that comprises a heterologous polynucleotide encoding the recombinant polypeptide and that does not express LDHA and/or LDHB; and does not express one, two, three or four of PDK1, PDK2, PDK3 and PDK4, wherein the cells produce no detectable lactate, whereby the yield of recombinant polypeptide is increased in comparison to the yield of recombinant polypeptide produced by a wild-type cell or a control mammalian cell having lactate dehydrogenase and/or pyruvate dehydrogenase kinase activity. In some embodiments, the production of recombinant polypeptide is increased by at least about 10%, e.g., at least about 15%, 20%, 25%, 30%, 35%, 40%, 50%, 60%, 70%, 80%, 90%, 100%, 150%, 200%, 250%, 300%, 400%, 500%, 600%, 700%, 800%, 900%, 1000% higher, or more, in comparison to the yield of recombinant polypeptide produced by a wild-type cell or a control mammalian cell having lactate dehydrogenase and/or pyruvate dehydrogenase kinase activity With respect to the embodiments of the methods, in some embodiments, the base is not needed to control the pH of the culture. In some embodiments, the culture comprises accumulated added base at a concentration of less than about 5 mOsm/kg, e.g., less than about 4.5 mOsm/kg, 4 mOsm/kg, 3.5 mOsm/kg, or 3 mOsm/kg, after at least about 5 days of culture. In some embodiments, lactate is not detectable in the culture. In some embodiments, the cell density in the culture is at least about $13\times10^6$ cells/ml, e.g., at least about $14\times10^6$ cells/ml, $15\times10^6$ cells/ml, $16\times10^6$ cells/ml, $17\times10^6$ cells/ml, or higher. In some embodiments, the mammalian cell is a Chinese Hamster Ovary (CHO) cell.

Suitable cultured cells for the expression of a glycosylated polypeptide are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of Autographa californica NPV and the Bm-5 strain of *Bombyx mori* NPV, and such viruses may be used as the virus, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian cell lines include, but are not limited to, monkey kidney CV1 cells transformed by SV40 (COS-7, ATCC CRL 1651); human embryonic kidney cells (293 or 293 cells subcloned for growth in suspension culture, Graham et al., J. Gen Virol. 36:59 (1977)); baby hamster kidney cells (BHK, ATCC CCL 10); Chinese hamster ovary cells/DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and human hepatoma cells (Hep G2).

Host cells are transformed with the above-described expression or cloning vectors for polypeptide production and cultured in conventional nutrient media modified as appropriate for inducing promoters, selecting transformants, or amplifying the genes encoding the desired sequences.

Promoters are well known in the art. Any promoter that functions in the host cell can be used for expression of the one or more polypeptides of interest, e.g., a therapeutic polypeptide, e.g., an antibody or fragment thereof, an enzyme, a cytokine, a hormone, in the mammalian cells described herein. Virtually any promoter capable of driving expression of a recombinant heterologous polypeptide of interest is suitable in the present mammalian cells including, but not limited to, U6, H1, CYC1, HIS3, GAL1, GAL4, GAL10, ADH1, PGK, PHO5, GAPDH, T7, CMV, SV40, and EF1a.

The host cells used to produce the polypeptide used in the methods described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), (Sigma), or GIBCO™ Dulbecco's Modified Eagle Medium: Nutrient Mixture F-12 (Invitrogen) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Other defined or synthetic growth media may also be used, and the appropriate medium for growing a specific type of host cells are known by one of skill in the art of molecular and cell biology. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™, hygromycin), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Standard cell culture conditions can be used to culture the cells. Cells are grown and maintained at an appropriate temperature, gas mixture, and pH (such as at about 20° C. to about 37° C., at about 5% to about 84% CO2, and at a pH between about 5 to about 9). In some embodiments, cells are grown in an appropriate cell medium at 37° C. for the first 48 hours, and shifted to 33° C. for the next 12 days. Reactions may be performed under aerobic or anoxic conditions based on the requirements of the host cells. In some embodiments, the cells are grown using any known mode of fermentation, including, but not limited to, batch, fed-batch, or continuous processes.

When using recombinant techniques, the polypeptide can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration. Where the polypeptide is secreted into the medium, supernatants from such expression systems are generally first concentrated using a commercially available protein concentration filter, for example, an Amicon or Millipore Pellicon ultrafiltration unit.

7. Methods of Increasing Production of Recombinant Polypeptide

Further provided are methods of increasing the production of a recombinant polypeptide. In varying embodiments, the methods comprises culturing a population of cells under conditions that allow the cells to produce the recombinant polypeptide, wherein each cell in the population is a mammalian cell that comprises a heterologous polynucleotide encoding the recombinant polypeptide and that does not express LDHA and/or LDHB; and does not express one, two, three or four of PDK1, PDK2, PDK3 and PDK4, wherein the cells produce no detectable lactate, whereby the yield of recombinant polypeptide is increased in comparison to the yield of recombinant polypeptide produced by a wild-type cell or a control mammalian cell having lactate dehydrogenase and/or pyruvate dehydrogenase kinase activity. In varying embodiments, the genes for LDHA and/or LDHB; and the genes one, two, three or four of PDK1, PDK2, PDK3 and PDK4 are homozygously knock-out, eliminated and/or rendered non-functional.

In varying embodiments, the population of mammalian cells devoid of lactate dehydrogenase activity have a polypeptide productivity of about 10% to about 1000% higher than cultured mammalian cells having detectable lactate dehydrogenase and/or pyruvate dehydrogenase kinase activity. In some embodiments, the cultured cells have a polypeptide productivity of at least about 10%, e.g., at least about 15%, 20%, 25%, 30%, 35%, 40%, 50%, 60%, 70%, 80%, 90%, 100%, 150%, 200%, 250%, 300%, 400%, 500%, 600%, 700%, 800%, 900%, 1000% higher, or more, than cultured cells having detectable lactate dehydrogenase and/or pyruvate dehydrogenase kinase activity.

8. Kits

Further provided are kits comprising a viable mammalian cell or a population of viable mammalian cells, each cell in the population being completely and absolutely devoid of lactate dehydrogenase activity, as described above and herein. In varying embodiments, the viable mammalian cell or a population of viable mammalian cells completely and absolutely do not express (i.e., are devoid of expression of) any of (i.e., express none of): LDHA and/or LDHB; and further do not express one, two, three or four of PDK1, PDK2, PDK3 and PDK4. In varying embodiments of the cells, the genes for: i) LDHA and/or LDHB; and the genes for ii) one, two, three or four of PDK1, PDK2, PDK3 and PDK4 are not expressed, rendered non-functional, eliminated and/or homozygously knocked out. In some embodiments, the cell or each member of the population of cells is a Chinese Hamster Ovary (CHO) cell.

EXAMPLES

The following examples are offered to illustrate, but not to limit the claimed invention.

Example 1

Production of Mammalian Cells Devoid of Lactate Dehydrogenase Activity

We knocked out 5 genes employing CRISPR/Cas9: PDK1, 2, 3, and 4 as well as LDHA. LDHB was not expressed in the cell lines used, but guide RNAs were designed and used for LDHB when implemented in a human cell line. Under normal metabolism, if oxidative metabolism is saturated, the cell maintains homeostasis by secreting lactate. This process is activated by a negative feedback loop in which products of the Pdh enzyme (at the entry of the TCA cycle) inhibit Pdh activity (FIG. 1), causing accumulation of pyruvate. This accumulation is normally relieved by the activity of Ldh, which converts pyruvate to lactate. Without being bound to theory, it has been generally hypothesized that without a knockout of Pdk, a knockout of LDHA and/or LDHB should inhibit growth since it causes pyruvate to accumulate without an alternative consumption route, leading to reduced growth or cell death. All previous evidence has suggested that, consistent with this, LdhA cannot be knocked out in CHO cells. We demonstrate that a knockout of all 4 Pdks removes the negative feedback loop leading to Pdh inhibition, allowing pyruvate to be freely converted to acetyl-CoA. The data show that by knocking out all 4 Pdks, we successfully deleted LDHA (LDHB was also not expressed) and completely eliminated lactate production in viable mammalian cells.

Figure 2:
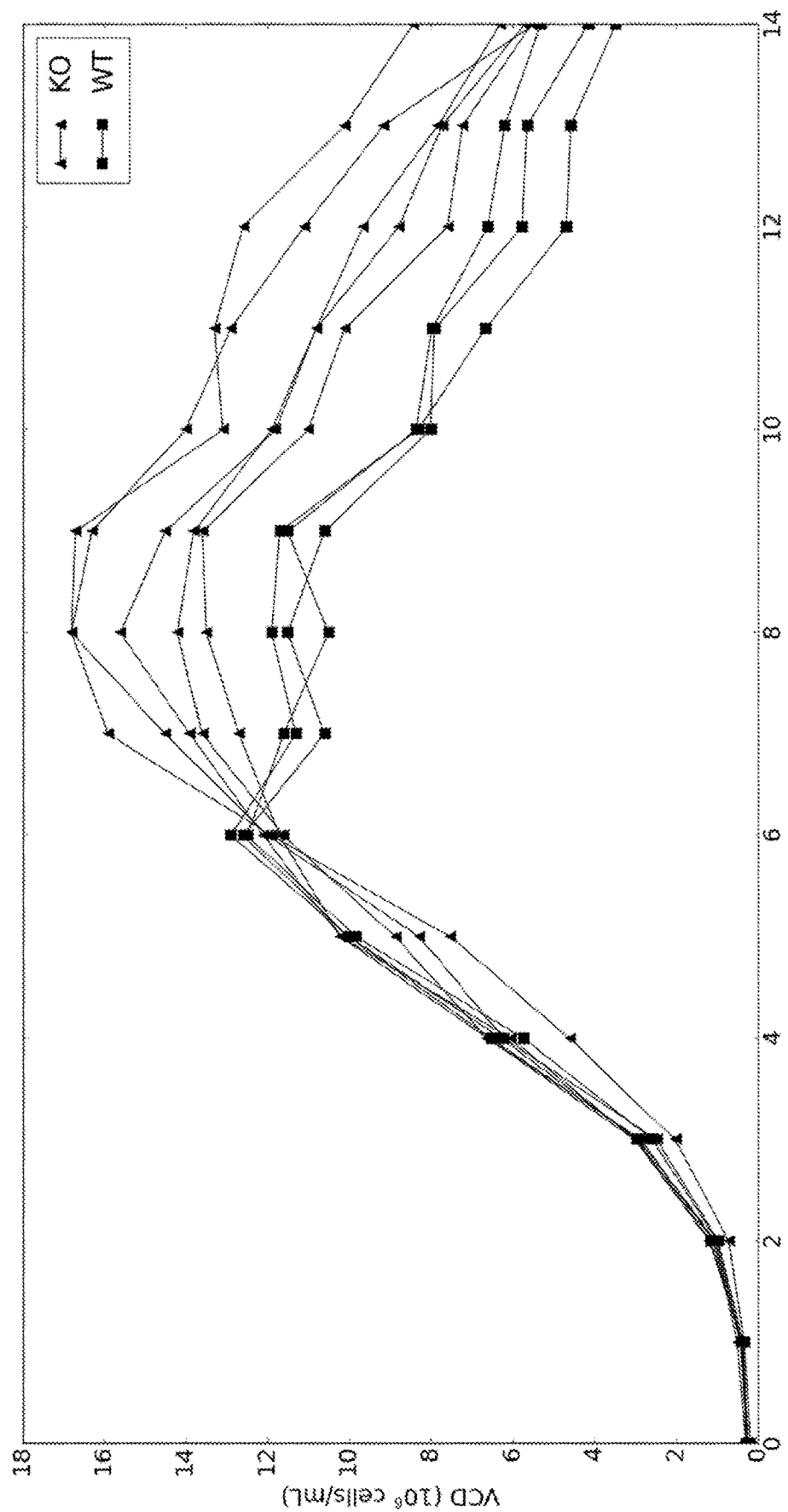
FIG. 2 illustrates viable cell density profile of wildtype and knockout cells grown in fed-batch. By day 6 the wildtype cultures began to die, but the knockout cell lines continued to grow until nutrients were exhausted.
Figure 3:
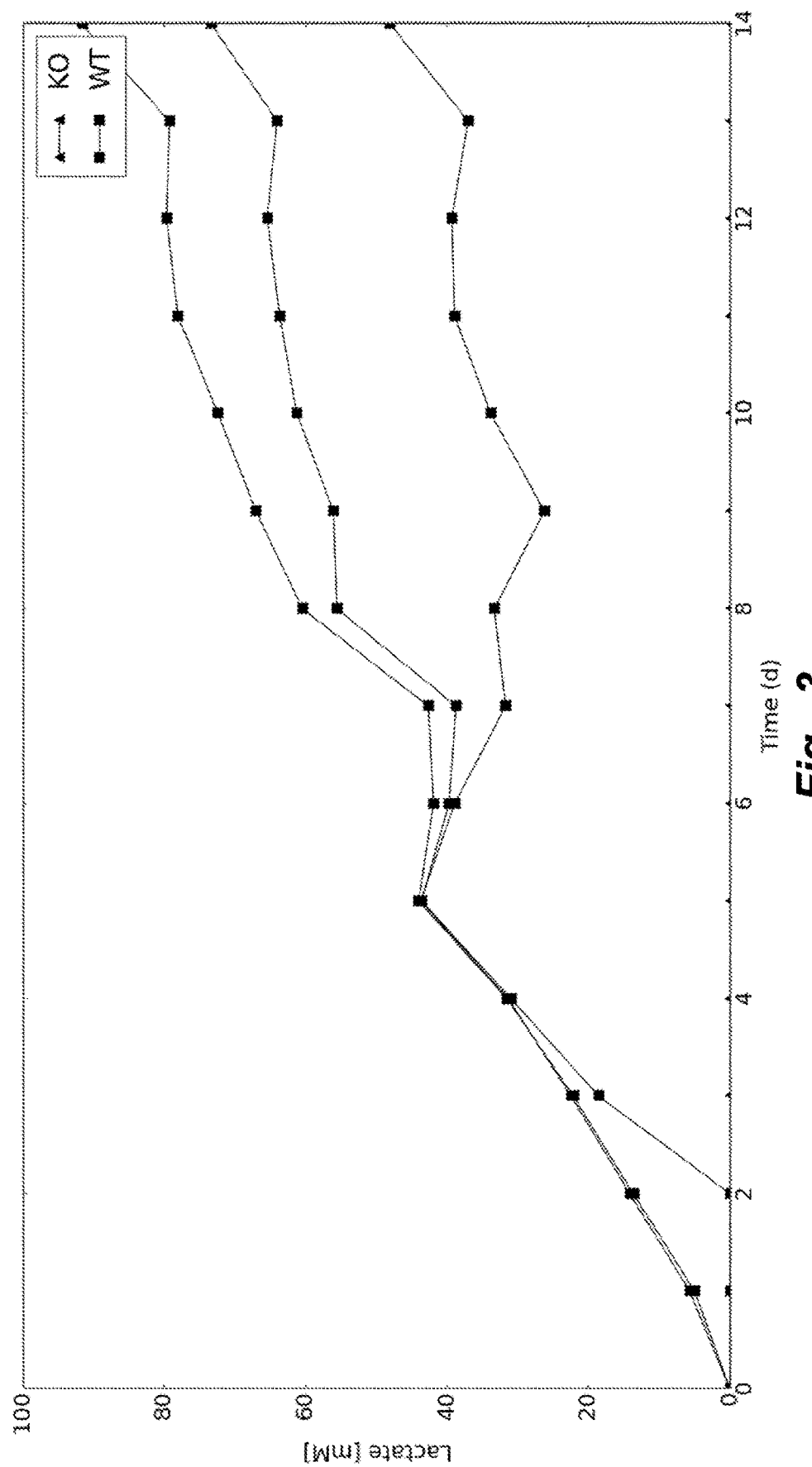
FIG. 3 illustrates a lactate concentration profile of wildtype and knockout cells grown in fed-batch. Wildtype cells elicited a steady increase in lactate concentration, while knockout cells saw no accumulation.
Figure 4:
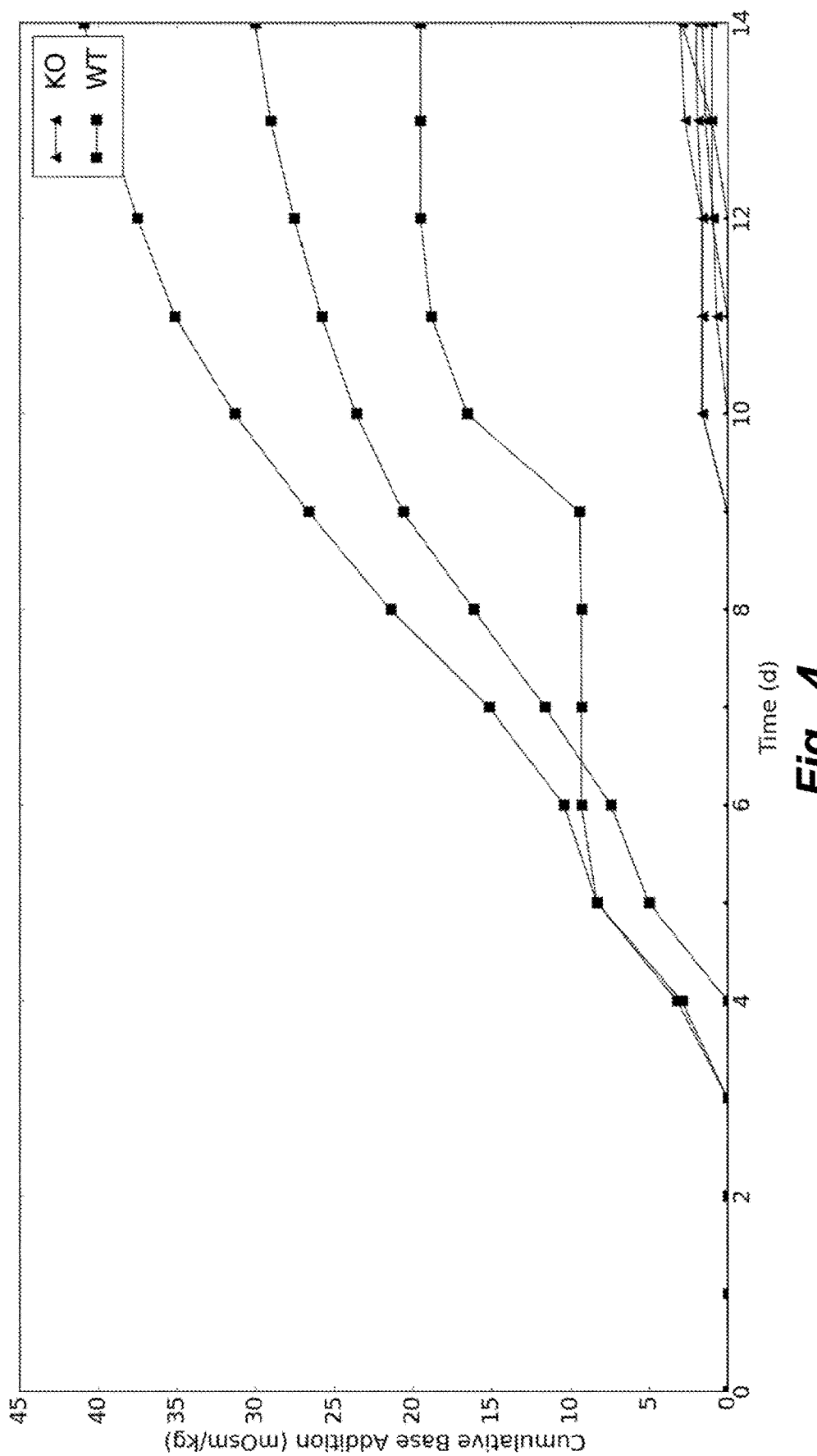
FIG. 4 illustrates base addition for wildtype and knockout cells grown in fed-batch. The lack of lactate production (or production of other organic acids) in the knockout cells allowed for a stable pH in the culture medium. Thus, base was not needed to control the pH.
Figure 5:
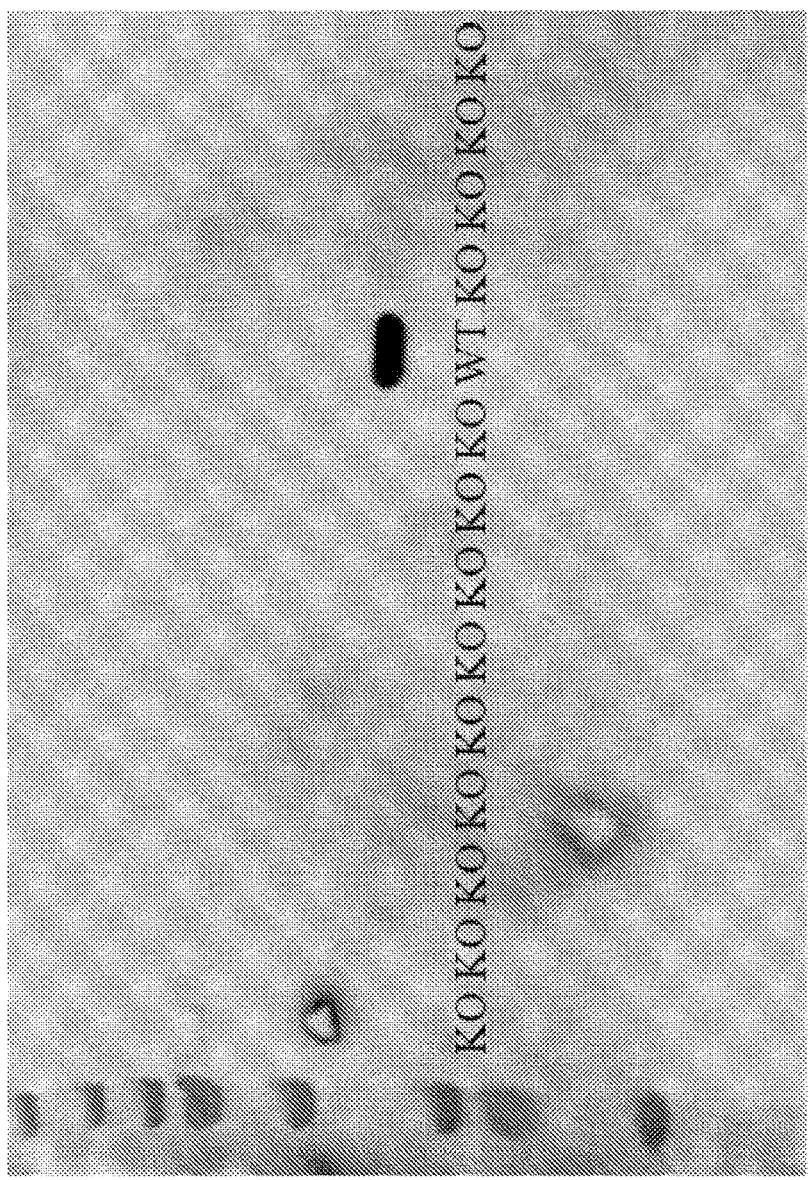
FIG. 5 illustrates that all Ldha knockout clones do not express the native Ldha protein. Shown are western blots for Ldha in all knockout clones. The blot on the left is for clones with all Pdks knocked out while the blot on the right is clones with only a subset of Pdks knocked out.
Figure 5:
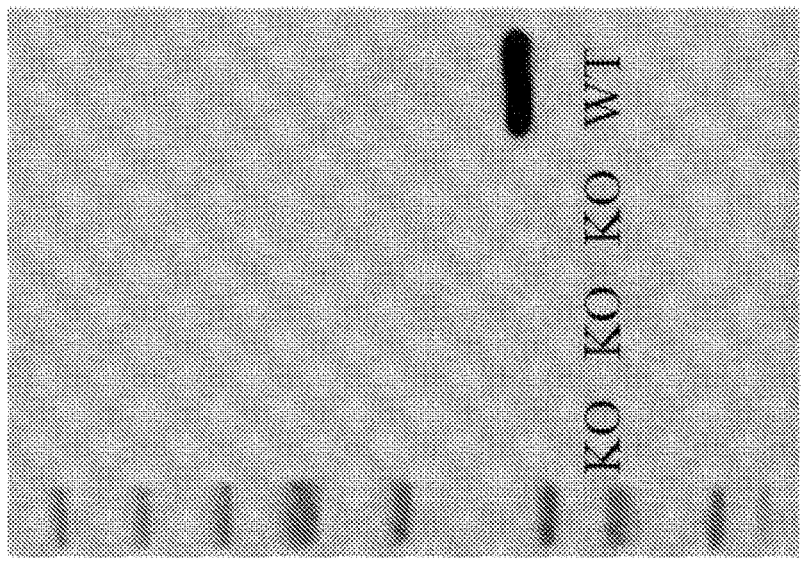
Figure 6:
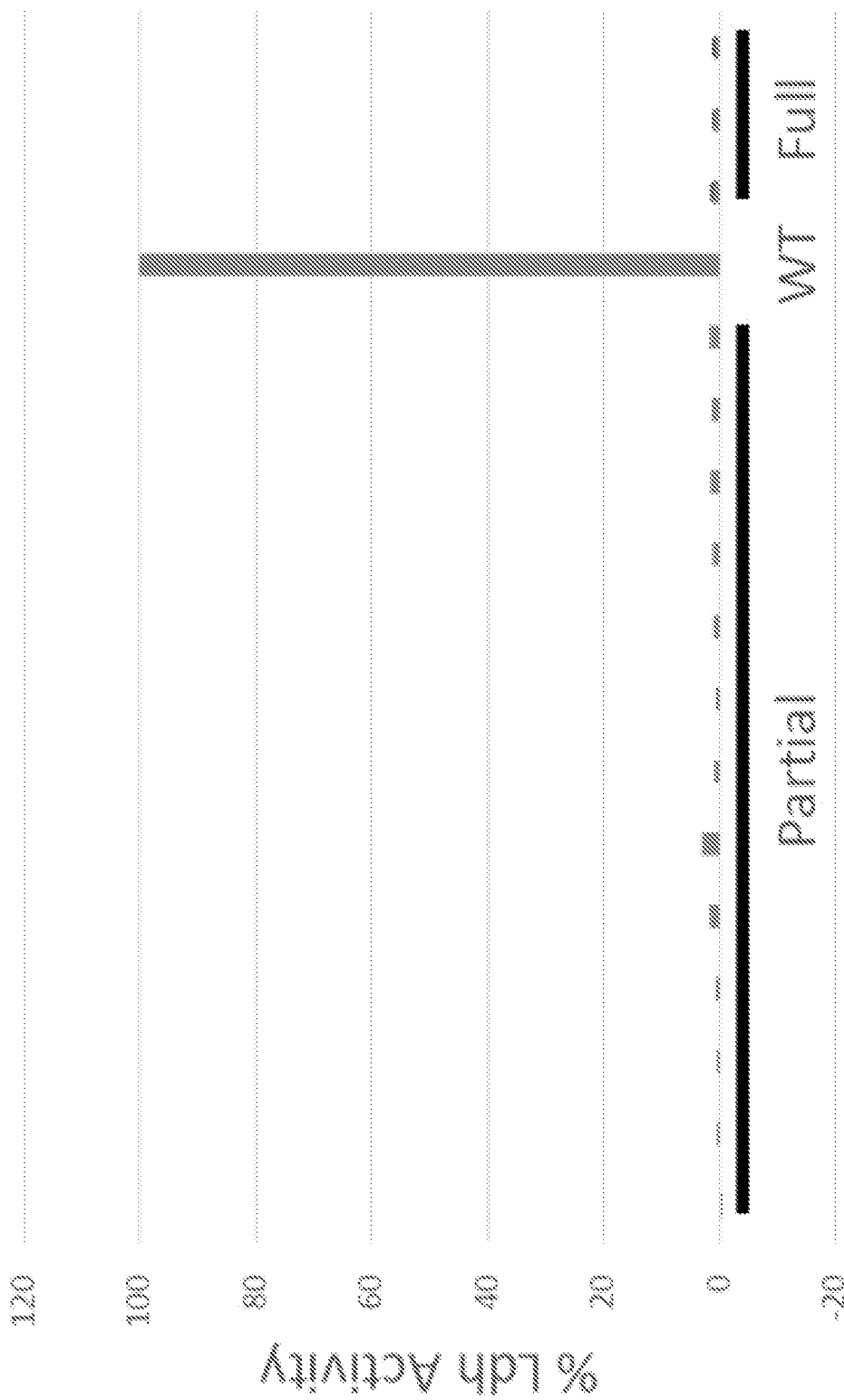
FIG. 6 illustrates that all mutants with 1-3 Pdk genes knocked out (Partial) and all 4 Pdk genes knocked out (Full) showed a complete elimination of Ldh activity.

By knocking out all 5 genes simultaneously (PDK1-4, LDHA), the mammalian PDK1-4/LDHA knockout cells can grow at rates similar to the wildtype cells while reaching higher maximum cell densities (FIG. 2). The PDK1-4/LDHA knockout cells do not produce any detectable lactate (FIG. 3), which allows for a vast decrease in the amount of base addition needed to maintain optimal pH levels (FIG. 4); this keeps the osmolarity low, which is also beneficial to the cells. Additionally, when assayed for lactate dehydrogenase activity, the knockouts showed none (FIGS. 5 and 6).

Example 2

Impact On Specific Productivity And Product Titer

To assess the impact of the LDHA knockout on the production of a recombinant protein, we obtained a Rituximab-producing cell line and used it for engineering. sgRNAs for all 4 Pdk genes and LDHA were simultaneously introduced with Cas9. Clones producing no lactate were selected and expanded, and the best performing clone (henceforth referred to as "KO") was used for further experiments. In parallel, Cas9 was introduced alone into the parental line, and clones were expanded. The best performing clone (henceforth referred to as Mock) was used for experiments to act as an experimental control.

Figure 7:
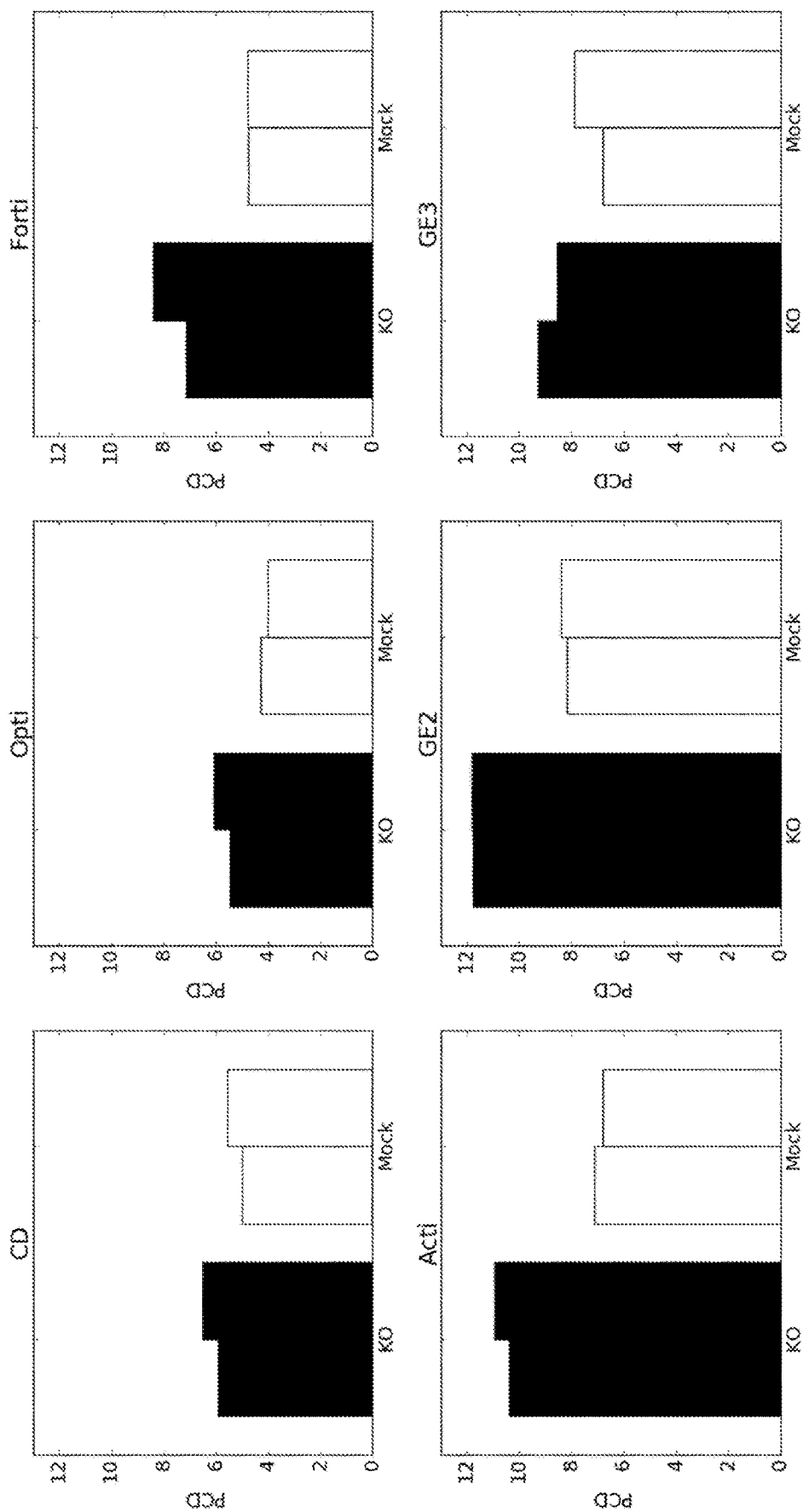
FIG. 7 illustrates testing different basal media (CD-CHO, OptiCHO, FortiCHO, ActiCHO, and 2 formulations from GE) in batch conditions to determine media useful for subsequent testing of expression of heterologous recombinant proteins. KO clones showed increased specific productivity (picograms per cell per day, PCD) compared to Mock clones in all media tested (2 biological replicates). ActiCHO and GE2 media showed the highest PCD.

Different basal media (CD-CHO, OptiCHO, FortiCHO, ActiCHO, and 2 formulations from GE) were tested in batch conditions to determine media useful for subsequent testing. KO clones showed increased specific productivity (picograms per cell per day, PCD) compared to Mock clones in all media tested (2 biological replicates). ActiCHO and GE2 media showed the highest PCD. Results are depicted in FIG. 7.

Figure 8:
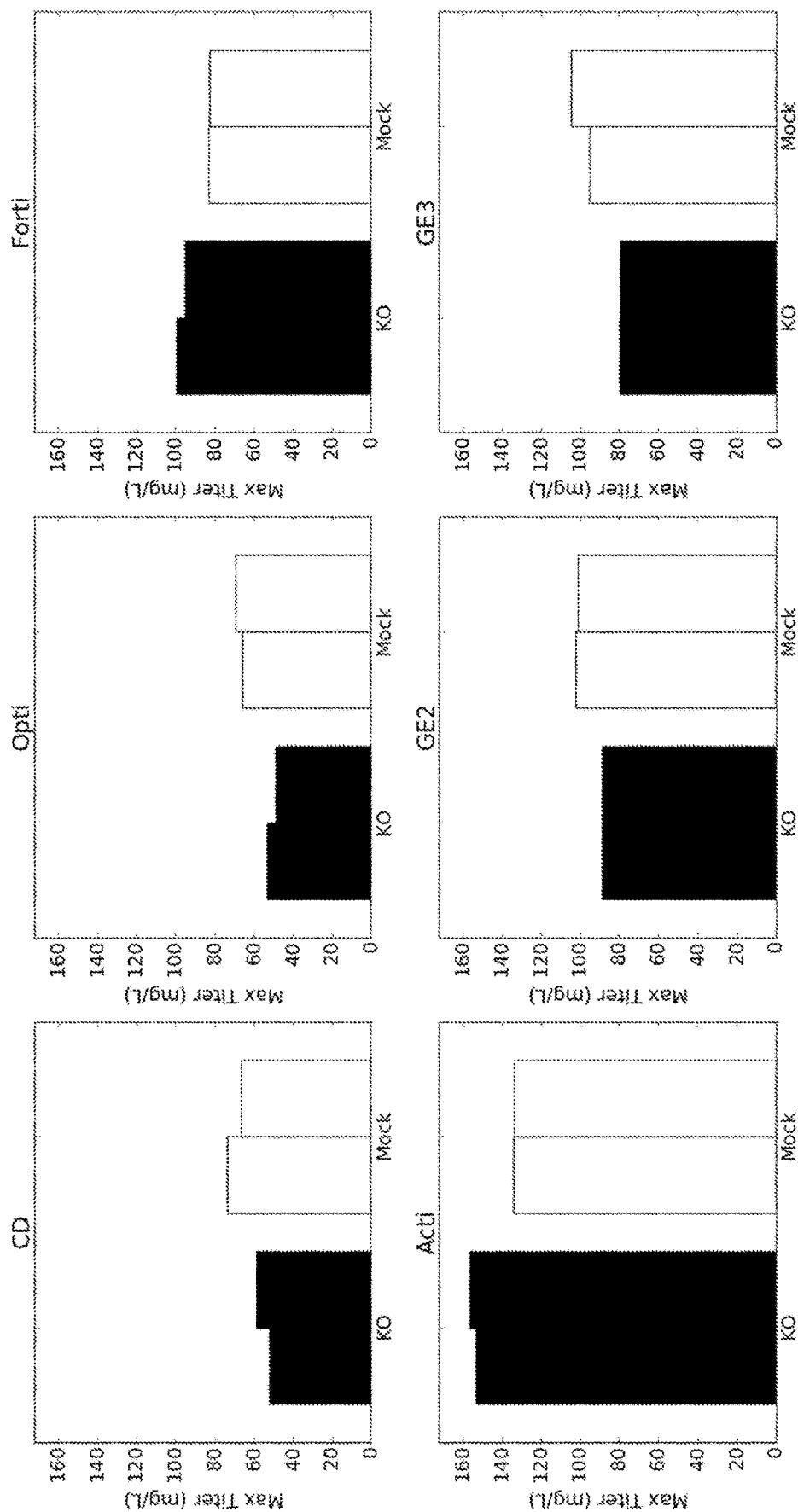
FIG. 8 illustrates that the base media ActiCHO proved to be the best media formulation when looking at maximum titer achieved during batch. Further, the KO cells showed increased performance compared to the Mock clones (2 biological replicates).

While ActiCHO and GE2 were similar in specific productivity, ActiCHO proved to be the best media formulation when looking at maximum titer achieved during batch. Again, the KO cells showed increased performance compared to the Mock clones (2 biological replicates). The results are depicted in FIG. 8.

Figure 9:
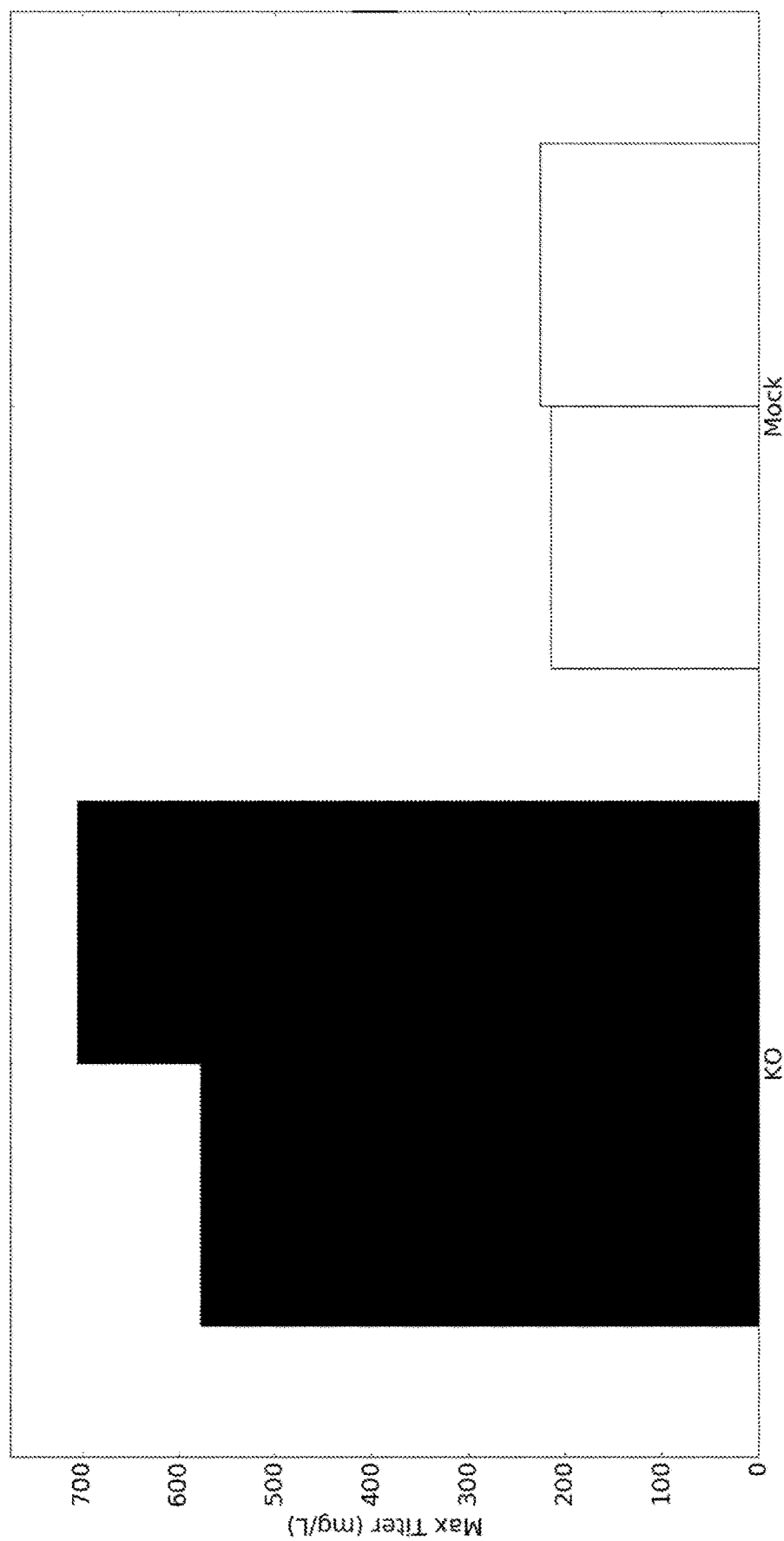
FIG. 9 illustrates KO clones producing nearly threefold more recombinant heterologous protein (here, Rituximab) compared to Mock clones when grown in fed-batch.
Figure 10:
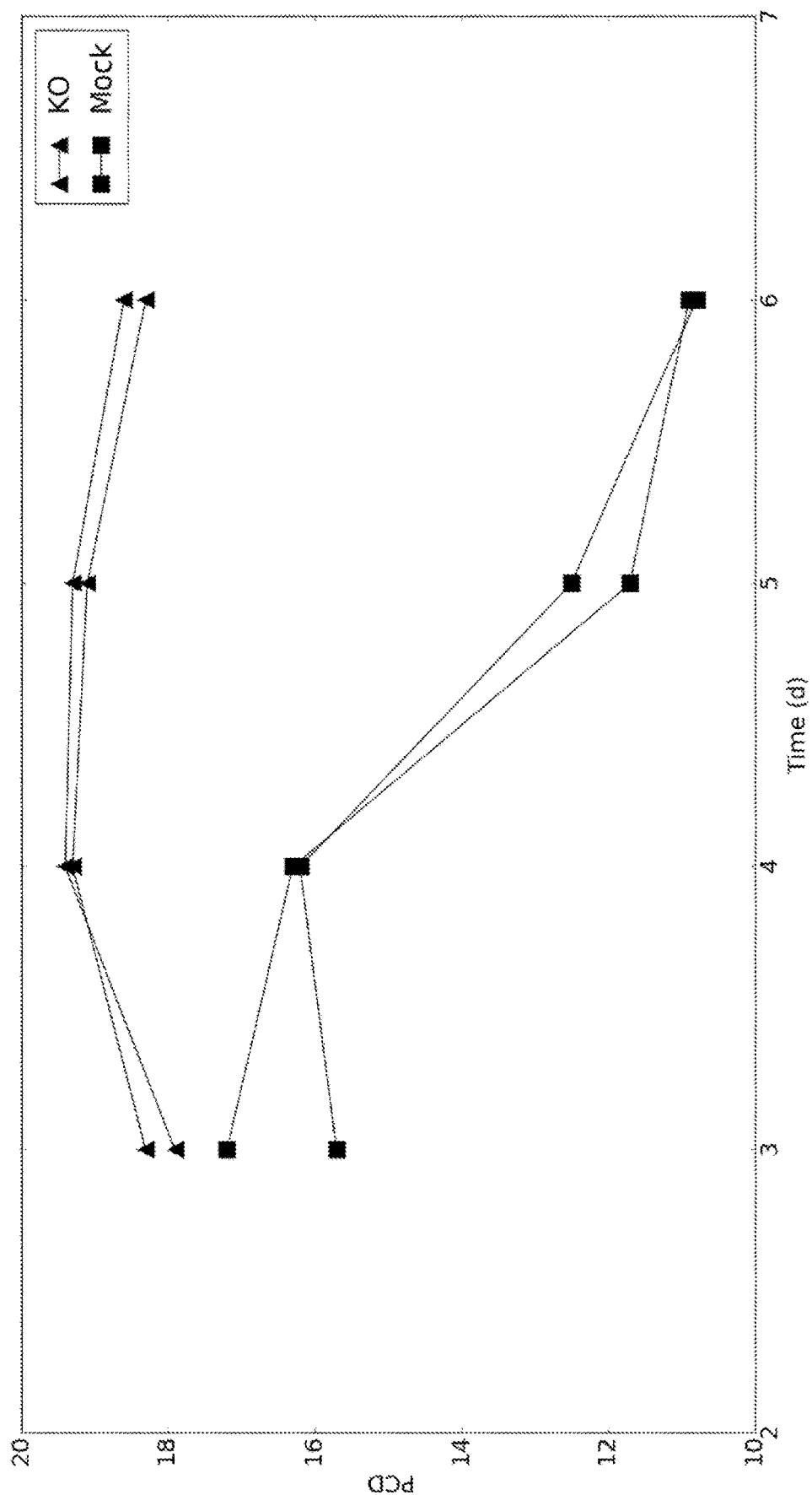
FIG. 10 illustrates that during fed-batch, over the course of the growth phase, specific productivity for KO clones remained consistently higher than that of Mock clones.

KO and Mock clones (2 replicates) were subsequently grown in fed-batch conditions in ambr15 bioreactors. ActiCHO was used as the basal media and different nutrient feeds and feeding strategies evaluated. The strategy with highest titers resulted in KO clones producing nearly three-fold more protein compared to Mock clones. The results are depicted in FIG. 9. FIG. 10 shows that, over the course of the growth phase, specific productivity for KO clones remained consistently higher than that of Mock clones.

Example 3

PDK Necessity/Sufficiency For LDHA Knockout

We attempted to knockout LDHA while knocking out only a subset of the four Pdk genes. Complete knockout of the following combinations was observed with complete knockout of LDHA and no lactate production:
PDK2
PDK1, PDK4
PDK2, PDK4
PDK1, PDK2, PDK4
PDK2, PDK3, PDK4

Partial knockouts of individual Pdk genes were also observed, but partial gene knockouts were always in addition to one of the aforementioned genotypes (e.g., a PDK2 full knockout with a partial PDK1 knockout also permitted full LDHA knockout with no lactate production, with LDHB also not expressed).

Figure 11:
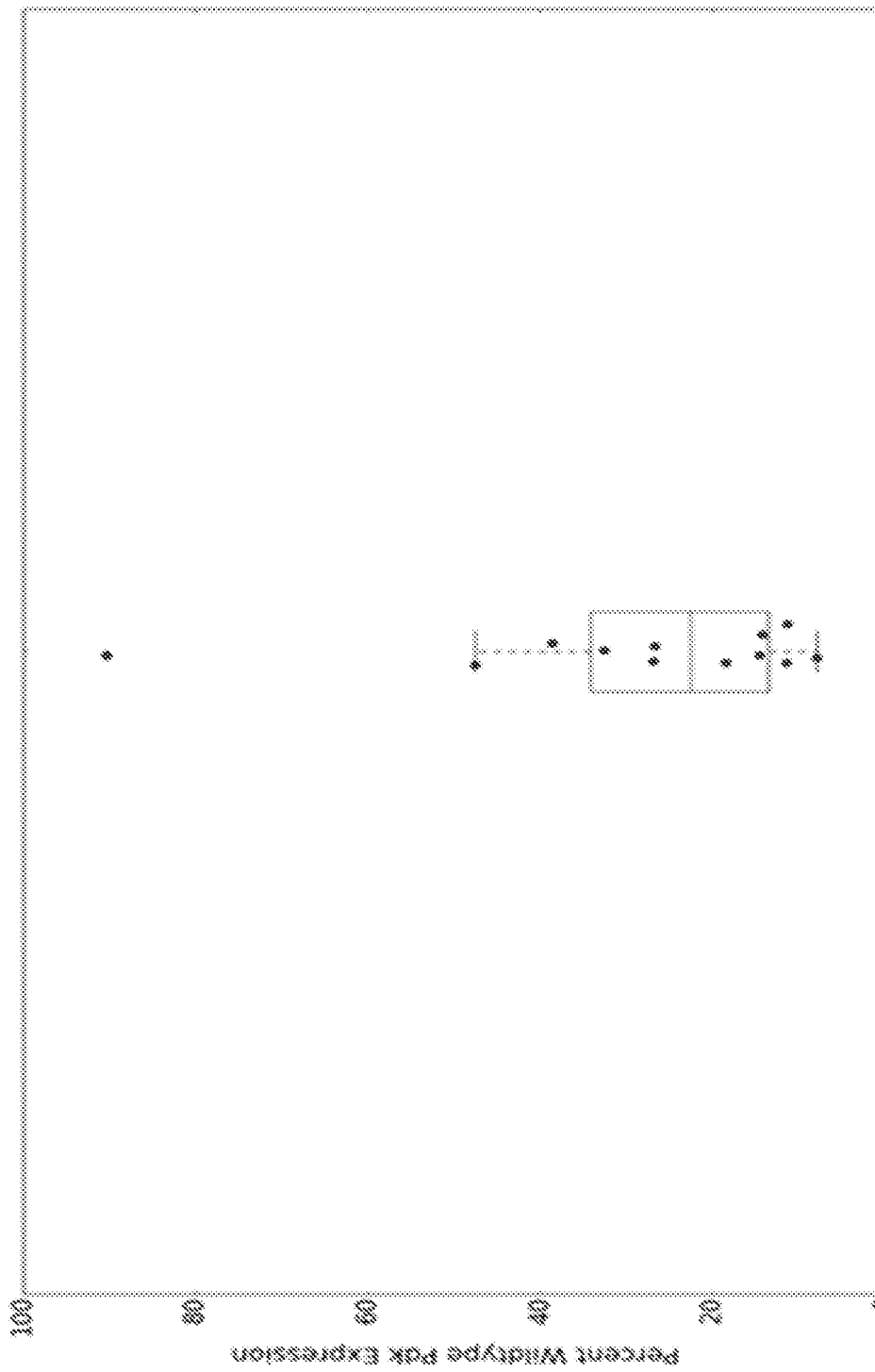
FIG. 11 illustrates that all clones in which not all Pdk genes were knocked out demonstrated a significant reduction of total expression of the Pdk genes, compared to total Pdk expression in wildtype cells.

FIG. 11 shows that all clones in which not all Pdk genes were knocked out demonstrated a significant reduction of total expression of the Pdk genes, compared to total Pdk expression in wildtype cells.

Figure 12:
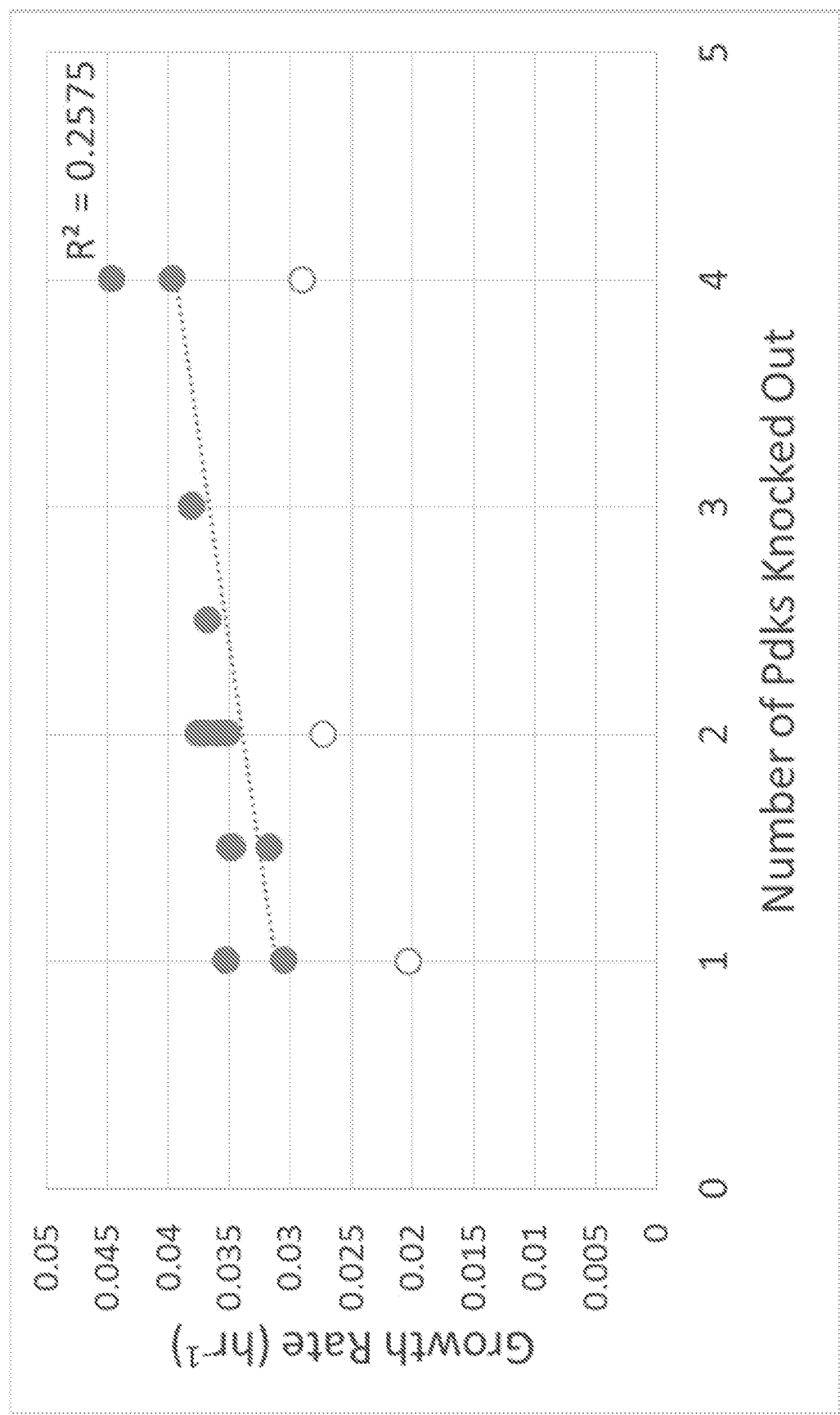
FIG. 12 illustrates that that the number of Pdks knocked out in addition to Ldha impacts the growth rate of the clones. There is a statistically significant ($p=0.0376$, $R^2=0.2575$) trend toward increased growth rate when more of the Pdks are knocked out, possibly as a result of decreased inhibition on Pdh, permitting increased flux into energetic pathways.
Figure 13:
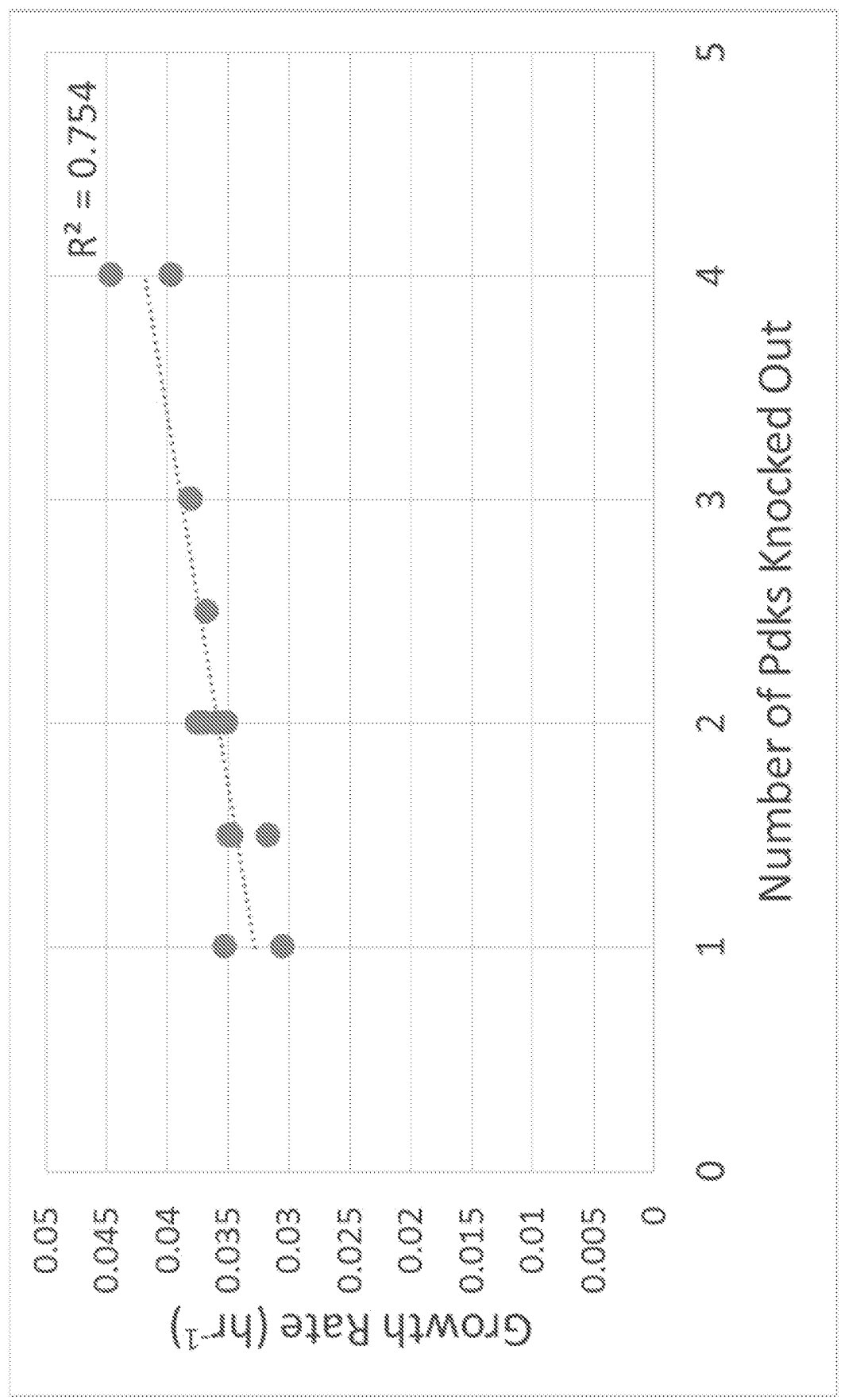
FIG. 13 illustrates that the trend toward increased growth rate with more of the Pdks knocked out is even more pronounced ($p=5.6e-5$, $R^2=0.754$) when clones exhibiting severely decreased growth (marked with unfilled circles in FIG. 12) are excluded from analysis.

We grew all clones with complete knockout of Ldha in batch culture to see if there were phenotypic differences between the clones corresponding to the number of Pdks knocked out in each line. Clones with fewer Pdks knocked out exhibited decreased growth rate when compared to the clones with all 4 Pdks knocked out (FIGS. 12 and 13). The highest growth levels were achieved when all 4 Pdks genes were knocked out.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A viable mammalian cell devoid of lactate dehydrogenase activity, wherein the genes for:
   (i) lactate dehydrogenase A (LDHA) and lactate dehydrogenase B (LDHB); and
   (ii) one or more of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4);
   are not expressed, rendered non-functional, eliminated and/or homozygously knocked out.

2. The mammalian cell of claim 1, wherein the genes for:
   i) lactate dehydrogenase A (LDHA) and lactate dehydrogenase B (LDHB); and
   ii) two or more of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out.

3. The mammalian cell of claim 2, wherein the genes for:
PDK1 and PDK2;
PDK1 and PDK3;
PDK1 and PDK4;
PDK2 and PDK3;
PDK2 and PDK4; or
PDK3 and PDK4
are not expressed, rendered non-functional, eliminated and/or homozygously knocked out.

4. The mammalian cell of claim 1, wherein the genes for:
i) lactate dehydrogenase A (LDHA) and lactate dehydrogenase B (LDHB); and
ii) three or more of pyruvate dehydrogenase kinase 1 (PDKI), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out.

5. The mammalian cell of claim 4, wherein the genes for:
PDK1, PDK2 and PDK3;
PDK1, PDK2 and PDK4;
PDK1, PDK3 and PDK4; or
PDK2, PDK3 and PDK4;
are not expressed, rendered non-functional, eliminated and/or homozygously knocked out.

6. The mammalian cell of claim 1, wherein the genes for:
i) lactate dehydrogenase A (LDHA) and lactate dehydrogenase B (LDHB); and
ii) all of pyruvate dehydrogenase kinase 1 (PDK1), pyruvate dehydrogenase kinase 2 (PDK2), pyruvate dehydrogenase kinase 3 (PDK3), and pyruvate dehydrogenase kinase 4 (PDK4) are not expressed, rendered non-functional, eliminated and/or homozygously knocked out.

7. The mammalian cell of claim 1, wherein the cell is a Chinese Hamster Ovary (CHO) cell.

8. The mammalian cell of claim 1, wherein the cell further comprises one or more heterologous polynucleotides encoding one or more recombinant polypeptides of interest.

9. A population of cells, wherein each cell in the population is a mammalian cell of claim 1.

10. An in vitro cell culture comprising a population of cells of claim 9.

11. A method of making a viable mammalian cell devoid of lactate dehydrogenase activity, comprising homozygously knocking out, rendering non-functional, and/or eliminating in the cell the genes for LDHA and LDHB, and the genes for one or more of PDK1, PDK2, PDK3 and PDK4.

12. The method of claim 11, comprising homozygously knocking out, rendering non-functional, and/or eliminating in the cell the genes for LDHA and LDHB, and the genes for two or more of PDK1, PDK2, PDK3 and PDK4.

13. The method of claim 12, wherein the genes for:
i) PDK1 and PDK2;
ii) PDK1 and PDK3;
iii) PDK1 and PDK4;
iv) PDK2 and PDK3;
v) PDK2 and PDK4; or
vi) PDK3 and PDK4
are not expressed, rendered non-functional, eliminated and/or homozygously knocked out.

14. The method of claim 11, wherein the genes for:
i) PDK1, PDK2 and PDK3;
ii) PDK1, PDK2 and PDK4;
iii) PDK1, PDK3 and PDK4; or
iv) PDK2, PDK3 and PDK4;
are not expressed, rendered non-functional, eliminated and/or homozygously knocked out.

15. The method of claim 11, comprising homozygously knocking out, rendering non-functional, and/or eliminating in the cell the genes for LDHA and LDHB, and the genes for all of PDK1, PDK2, PDK3 and PDK4.

16. A method for eliminating lactate production in cultured mammalian cells, the method comprising culturing a population of cells of claim 9, wherein the cells produce no detectable lactate.

17. A method of producing a recombinant polypeptide, comprising culturing a population of cells under conditions that allow the cells to produce the recombinant polypeptide, wherein each cell in the population is a mammalian cell of claim 8.

18. A method of increasing the production of a recombinant polypeptide, comprising culturing a population of cells under conditions that allow the cells to produce the recombinant polypeptide, wherein each cell in the population is a mammalian cell of claim 8, whereby the yield of recombinant polypeptide is increased in comparison to the yield of recombinant polypeptide produced by a wild-type cell or a control mammalian cell having lactate dehydrogenase and/or pyruvate dehydrogenase kinase activity.

19. The method of claim 11, wherein the mammalian cell is a Chinese Hamster Ovary (CHO) cell.

* * * * *